United States Patent
Mabotuwana et al.

(10) Patent No.: US 10,354,049 B2
(45) Date of Patent: Jul. 16, 2019

(54) AUTOMATIC DETECTION AND RETRIEVAL OF PRIOR ANNOTATIONS RELEVANT FOR AN IMAGING STUDY FOR EFFICIENT VIEWING AND REPORTING

(71) Applicant: KONINKLIJKE PHILIPS N.V., Eindhoven (NL)

(72) Inventors: Thusitha Dananjaya De Silva Mabotuwana, Yonkers, NY (US); Yuechen Qian, Briarcliff Manor, NY (US); Merlijn Sevenster, New York, NY (US); Gabriel Ryan Mankovich, Yorktown Heights, NY (US)

(73) Assignee: Koninklijke Philips N.V., Eindhoven (NL)

( * ) Notice: Subject to any disclaimer, the term of this patent is extended or adjusted under 35 U.S.C. 154(b) by 250 days.

(21) Appl. No.: 14/420,815

(22) PCT Filed: Aug. 12, 2013

(86) PCT No.: PCT/IB2013/056572
§ 371 (c)(1),
(2) Date: Feb. 10, 2015

(87) PCT Pub. No.: WO2014/030092
PCT Pub. Date: Feb. 27, 2014

(65) Prior Publication Data
US 2015/0205917 A1    Jul. 23, 2015

Related U.S. Application Data

(60) Provisional application No. 61/691,951, filed on Aug. 22, 2012.

(51) Int. Cl.
*G06K 9/00* (2006.01)
*G06F 19/00* (2018.01)
(Continued)

(52) U.S. Cl.
CPC .............. *G06F 19/321* (2013.01); *G06T 7/00* (2013.01); *G06T 11/60* (2013.01); *G16H 15/00* (2018.01); *G16H 50/70* (2018.01); *G06T 2210/41* (2013.01)

(58) Field of Classification Search
CPC ........ G06F 19/321; G06F 19/00; G06T 11/60; G06T 2210/41; G06T 7/00; G16H 15/00; G16H 50/70
(Continued)

(56) References Cited

U.S. PATENT DOCUMENTS 6,041,335 A    3/2000    Merritt et al.
7,184,582 B2   2/2007    Giger et al.
(Continued)

FOREIGN PATENT DOCUMENTS

CN    101396283 A    4/2009
EP    2302545 A2     3/2011
(Continued)

*Primary Examiner* — Tom Y Lu

(57) ABSTRACT

An annotation support system (10) comprising at least one display device (20). A context extraction module (24, 36) determines a context of a current medical image from a current image study. A matching module (26, 38) compares the context of the current medical image to contexts of prior medical images from prior image studies. A display module (28, 40) displays at least one of context relevant annotations and context relevant medical images from the prior image studies which match the context of the current medical study.

20 Claims, 4 Drawing Sheets

(51) Int. Cl.
*G06T 7/00* (2017.01)
*G06T 11/60* (2006.01)
*G16H 50/70* (2018.01)
*G16H 15/00* (2018.01)

(58) Field of Classification Search
USPC .......................................................... 382/128
See application file for complete search history.

(56) References Cited

U.S. PATENT DOCUMENTS

| | | | |
|---|---|---|---|
| 7,646,903 B2* | 1/2010 | Kaftan | G06K 9/6206 |
| | | | 341/79 |
| 7,865,815 B2 | 1/2011 | Albornoz et al. | |
| 8,077,946 B2 | 12/2011 | Akira | |
| 8,625,867 B2 | 1/2014 | Moriya | |
| 8,913,078 B2 | 12/2014 | Masumoto | |
| 2006/0239589 A1* | 10/2006 | Omernick | G06F 19/321 |
| | | | 382/293 |
| 2009/0080744 A1* | 3/2009 | Sagawa | G06F 19/321 |
| | | | 382/131 |
| 2009/0217150 A1 | 8/2009 | Lin | |
| 2009/0232378 A1* | 9/2009 | Nakamura | G06T 7/003 |
| | | | 382/131 |
| 2010/0080470 A1 | 4/2010 | Deluca et al. | |
| 2011/0073813 A1 | 3/2011 | Caldwell et al. | |
| 2011/0074813 A1* | 3/2011 | Masumoto | G06T 19/00 |
| | | | 345/629 |
| 2011/0075900 A1* | 3/2011 | Masumoto | G06F 19/321 |
| | | | 382/128 |
| 2015/0205917 A1 | 7/2015 | Mabotuwana et al. | |

FOREIGN PATENT DOCUMENTS

| | | |
|---|---|---|
| JP | 2003524492 A | 8/2003 |
| JP | 2005278786 A | 10/2005 |
| JP | 2009093544 A | 4/2009 |
| JP | 2011083591 A | 4/2011 |
| JP | 2012141797 A | 7/2012 |
| RU | 61442 U1 | 2/2007 |

* cited by examiner

AUTOMATIC DETECTION AND RETRIEVAL OF PRIOR ANNOTATIONS RELEVANT FOR AN IMAGING STUDY FOR EFFICIENT VIEWING AND REPORTING

CROSS-REFERENCE TO PRIOR APPLICATIONS

This application is the U.S. National Phase application under 35 U.S.C. § 371 of International Application No. PCT/IB2013/056572, filed on Aug. 12, 2013, which claims the benefit of U.S. Provisional Application No. 61/691,951, filed on Aug. 22, 2012. These applications are hereby incorporated by reference herein.

The present application relates generally to a system and method for annotating and/or retrieving content. It finds particular application in conjunction with the efficient retrieval of prior image studies relevant to a current study and will be described with particular reference thereto. However, it is to be understood that it also finds application in other usage scenarios and is not necessarily limited to the aforementioned application.

On a routine basis, radiologists work with an increasing number of images to diagnose and treat patients in an optimal manner. Patients, e.g. ones with cancers, frequently undergo imaging exams and over time accumulate numerous imaging studies in their medical records often pertaining to the same anatomical region. When a radiologist reads a current exam (s)he compares the current exam images with images from prior exams in order to determine changes in the lesions over time and discover if any new lesions exist. This process involves looking through a set of the patient's 2D/3D diagnostic images. As the images are viewed, a radiologist often marks a region (or regions) of interest (ROI) to indicate an area of importance using a set of annotation tools. During this process, radiologists also compare the current imaging study to prior imaging studies to determine the changes in size of a particular lesion and other details to understand the overall progress of the patient. Due to the high volume of images that need to be reviewed, it is extremely time consuming for a radiologist to identify and review all of the relevant prior studies for the patient. To reduce the number of images to review, it is common practice to compare only images (often only the 'key images') from the most recent relevant study (i.e., with the same modality and of body region) to images from the current study. A key drawback of this practice is that it becomes difficult to understand the overall change/progress over time since the temporal progression is not explicitly developed, and interpretation is up to the individual radiologist.

Additionally, if the radiologist identifies a lesion on a current image, he/she may go back to a prior study of the same patient, open an image viewer, identify images of the same patient region, and find images that provide similar views of the lesion(s) as the current image. Routinely, the radiologist marks the lesion on the current image for comparison. Finding prior images that provide similar views of a lesion for suitable comparison can be time-consuming. The lesion may not have been identified in the prior relevant image(s). Further, current radiology image viewing systems do not automatically detect prior, relevant studies related to a current ROI. Due to the absence of image linking on a specific basis, it is difficult for a radiologist to accurately determine the change/progress of a ROI over time.

The present application provides new and improved methods and system which overcome the above-referenced problems and others.

In accordance with one aspect, an annotation support system is provided. The system comprising at least one display device and at least one processor programmed to determine a context of a current medical image from a current image study, compare the context of the current medical image to contexts of prior medical images from prior image studies, and display at least one of context relevant annotations and context relevant medical images from the prior image studies which match the context of the current medical study.

In accordance with another aspect, a method of providing annotation support is provided. The method comprising determining a context of an annotation on a current medical image from a current image study, comparing the context of the current medical image to contexts of prior annotations and medical images from prior image studies, and displaying at least one of context relevant annotations and context relevant medical images from the prior image studies which match the context of the current medical study.

In accordance with another aspect, an annotation support system is provided. The system comprising at least one display device, context extraction module which determines a context of a current medical image from a current image study, a matching module which compares the context of the current medical image to contexts of prior medical images from prior image studies, and a display module which displays at least one of context relevant annotations and context relevant medical images from the prior image studies which match the context of the current medical study.

One advantage resides in providing a more efficient mechanism to annotate related images resulting in a more consistent set of annotated images due to annotation reuse.

Another advantage resides in increased workflow efficiency.

Another advantage resides in providing a more efficient mechanism to find and view related prior annotations of a lesion on the current image.

Still further advantages of the present invention will be appreciated to those of ordinary skill in the art upon reading and understanding the following detailed description.

The invention may take form in various components and arrangements of components, and in various steps and arrangement of steps. The drawings are only for purposes of illustrating the preferred embodiments and are not to be construed as limiting the invention.

Figure 1:
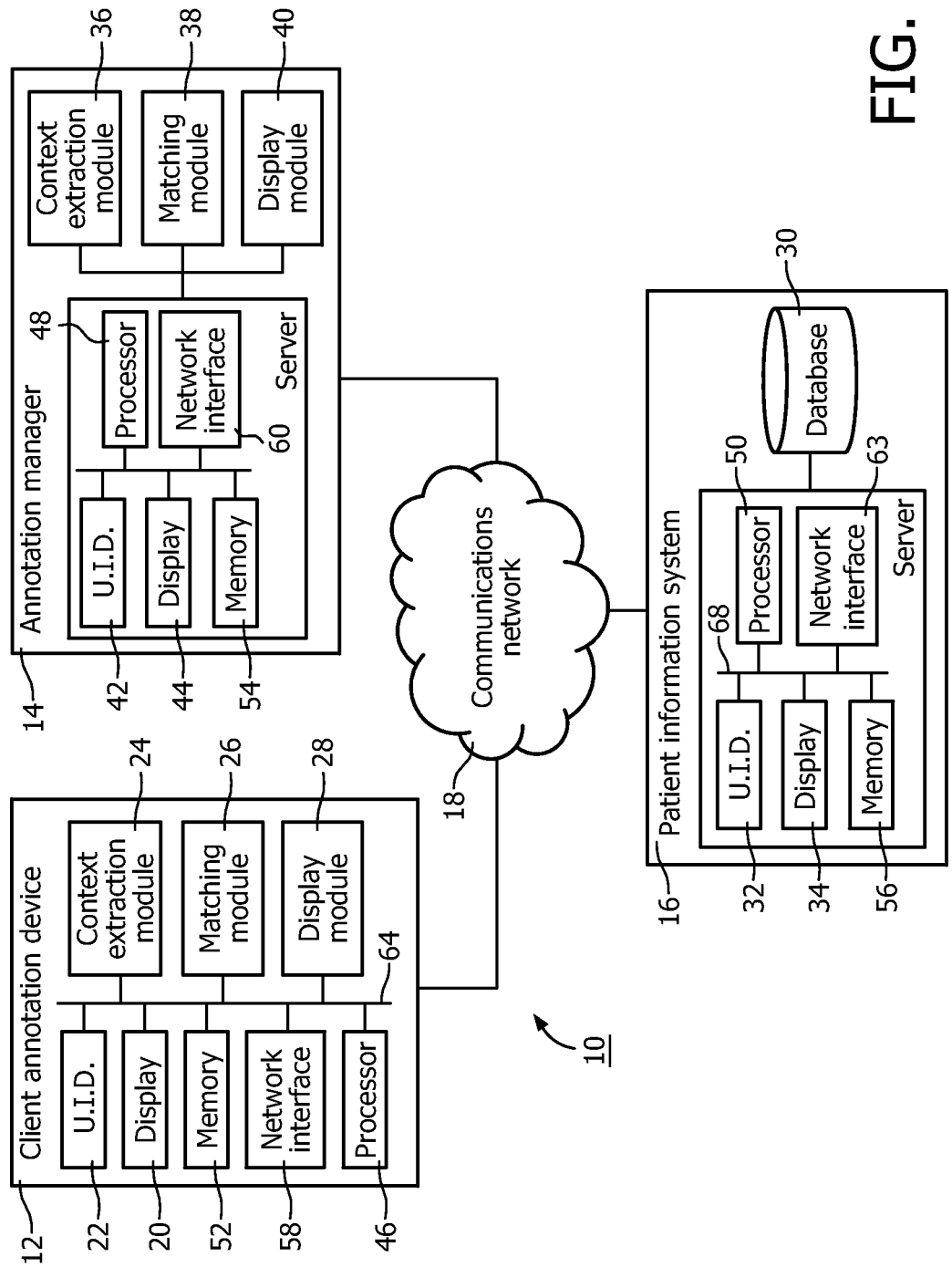
FIG. 1 illustrates a block diagram of an exemplary embodiment of an annotation support system according to aspects of the present application.

During medical imaging, one or more images are generated from scans of a patient. Types of medical images include magnetic resonance (MR or MRI), computed tomography (CT or CAT), X-ray, ultrasound, positron emission tomography (PET) images, single photon emission computed tomography (SPECT), and the like. After a scan has been completed, it is a common practice for a radiologist to annotate these images with information which provide descriptive or identifying information of the image. The annotations provide information relating to the context of the image, demographics of the image, such as an identification of the patient, type of examination, hospital, date of examination, type of acquisition, type of scan, the orientation of the image, the use of special image processing filter, statistics associated with regions of interest shown on the image, and/or the like. Typically, annotations include textual information, however, it should be appreciated that the annotation includes various visual information including shapes, dimensions, and the like of particular elements of an image.

The present disclosure provides an annotation support system 10 that enables a radiologist to locate and retrieve prior imaging studies and to review and reuse prior annotations from the prior studies with an imaging study currently under investigation. In current radiology workflow, each time a lesion needs to be annotated, the radiologist reviews prior studies of the same patient to find images that contain similar views of the lesion(s) as on the current image. Finding images that provide similar views of a lesion can be time-consuming. Radiologists usually annotate a few selected images (known as 'key images') with specific finding details (lesion measurements for instance) and often, these prior key-image annotations contain contextual information similar to the current images. The annotation support system 10 utilizes the contextual information from prior images to automatically find relevant prior annotations when viewing the current image. Such a system provides consistency between lesion annotations and increases workflow efficiency.

The annotation support system 10 further detects annotations automatically and semantically from prior reports when a new annotation is created and enables radiologists to easily compare similar findings. Findings on prior images are also linked when similar findings are observed, allowing a radiologist to monitor the progress of a lesion over time. In current radiology workflow, each annotation describing a finding is independent, making it difficult to monitor progress. Identifying the same region of interest across multiple studies for a given patient is currently a manual, time consuming effort. As a result, radiologists usually review only the most recent images which show only a limited view of the rate of progress (of a lesion for instance). The system 10 links findings for a given patient and displays a finding specific temporal view of the details while integrating well into the existing workflow. Such a system provides a better overall view of a finding's progress, potentially leading to better outcomes, and improved workflow efficiency due to the automatic retrieval of prior findings.

With reference to FIG. 1, the annotation support system 10 includes a client annotation device 12, optionally an annotation manager 14, a patient information system 16, and the like. Suitably, the components of the system 10 are interconnected through a communication network 18, such as the Internet, a local area network, a wide area network, a wireless network, or the like.

The client annotation device 12 displays one or more images of a patient and enables annotation of the one or more images with information providing descriptive or identifying information of the image. The one or more images and corresponding annotations are typically stored within the patient information system 16 which is accessed by the client annotation device 12 through the communication network 18. The annotations suitably include visual data indicative of the context of the image, demographics of the image, such as an identification of the patient, type of examination, hospital, date of examination, type of acquisition, type of scan, the location and orientation of the image, the use of special image processing filter, statistics associated with regions of interest shown on the image, and so on. The annotation can be generated manually and/or automatically. As to the former, a display 20 of the client annotation device 12 in conjunction with one or more input devices 22 enable a radiologist to annotate one or more images presented on the display 20. As to the latter, one or more prior annotations are provided to the user. For example, the client annotation device 12 automatically detects context sensitive annotations from prior related images based on current image context and enables the radiologist, for instance, to reuse these annotations or edit and reuse.

In order to accomplish this, the client annotation device 12 includes a context extraction module 24 which automatically determines the context of the current image on display. The context extraction module 24 also determines the context of prior images and/or annotations such as identification of the patient, the body part or organ being imaged, type of examination, hospital, date of examination, type of acquisition, type of scan, the orientation of the image. A matching module 26 of the client annotation device 12 compares the current image context to contexts of images from prior studies stored in the patient information system 16 and provides relevant prior context-sensitive annotations that were used in the prior studies to client annotation device 12. A display module 28 displays the relevant prior context-sensitive annotations to the radiologist through the display 20 of the client annotation device 12 for use in annotating the current image. The display module 28 also enables the radiologist to customize a list of prior annotations such that annotations are, for instance, from all prior studies the current radiologist has annotated instead of all relevant prior studies for the current patient (which may contain annotations from other radiologists). The relevant prior context-sensitive annotations can then be used in an application specific manner, for example, overlaying directly on the current image under investigation or being displayed as a list to the radiologist.

The client annotation device 12 also automatically detects relevant prior images when a new annotation is created. In order to accomplish this, the context extraction module 24 automatically extracts context information of a region of interest (ROI) on a current image. The context information can come from an imaging technician to describe the properties of the scan, the region scanned, etc. or can come from the diagnosing radiologist. The matching module 26 compares the current context information of the ROI on the current image to contexts of ROIs from prior studies stored in the patient information system 16 and provides relevant prior studies which include the same context information of the ROI on the current image. The display module 28 displays the relevant prior studies to the radiologist through the display 20 of the client annotation device 12. The display module 28 enables the radiologist to 'overlay' a current image slice over a corresponding prior image slice of the relevant prior study, providing a visual comparison of ROIs on the image itself and thereby any changes to the previous finding. The display modules 28 further provides a visual representation of ROI/finding specific details along a temporal axis.

The patient information system 16 stores the images and/or image annotations from the annotation support system 10, such as from the client annotation device 12, in one or more databases 30. For example, the patient information system 16 is a radiology information system (RIS) and/or picture archiving and communication system (PACS) which stores the images acquired from a medical imaging system and/or image annotations generated by the client annotation device 12. In some embodiments, the patient information system 14 also stores images and/or image annotations from a user input device 32 of the patient information system 16 in the databases 30 and/or allows stored images and/or image annotations to be viewed on a display device 34 of the patient information system 16. The display device 34 can additionally or alternatively be used to facilitate receipt of images and/or image annotations from the user input device 32. Examples of patient information systems include, but are not limited to, electronic medical record systems, departmental systems, and the like.

Optionally, the annotation support system 10 includes an annotation manager 14 which automatically provides context sensitive annotations from prior annotations and/or relevant prior images directly to the radiologist and/or the client annotation device 12. In performing this functionality, the annotation manager 14 and/or client annotation device 12, both be stand-alone devices, may work independently of each other or in cooperation. The annotation manager 14 includes a context extraction module 36 which determines the context of the current image on display on the client annotation device 12. The context extraction module 36 also determines the context of an annotation and stores the context information along with other annotation information to the patient information system 16. A matching module 38 of the annotation manager 14 compares the current image context to contexts of images from prior studies stored in the patient information system 16 and provides relevant prior context-sensitive annotations that were used in prior studies to client annotation device 12. A display module 40 of the annotation manager 14 displays the relevant prior context-sensitive annotations to the radiologist through the display 20 of the client annotation device 12. The display module 40 enables the radiologist to customize a list of prior annotations such that annotations are, for instance, from all prior studies the current radiologist has annotated instead of all relevant prior studies for the current patient (which may contain annotations from other radiologists). The relevant prior context-sensitive annotations can then be used in an application specific manner, for example, overlaying directly on the current image under investigation or being displayed as a list to the radiologist.

The annotation manager 14 also automatically detects relevant prior images when a new annotation is created. In order to accomplish this, the context extraction module 36 automatically extracts context information of a region of interest (ROI) on a current image of the client annotation device 12. The context information can come from an imaging technician to describe the properties of the scan, the region scanned, etc. or can come from the diagnosing radiologist. The matching module 38 compares the current context information of the ROI on the current image to contexts of ROIs from prior studies stored in the patient information system 16 and provides relevant prior studies which include the same or semantically similar context information of the ROI on the current image. The display module 40 displays the relevant prior studies to the radiologist through the display 20 of the client annotation device 12. The display module 40 enables the radiologist to 'overlay' a current image slice over a prior image slice of the relevant prior study, providing a visual comparison of ROIs on the image itself and thereby any changes to the previous finding. The display modules 40 further provides a visual representation of ROI/finding specific details along a temporal axis.

In some embodiments, the annotation manager 14 also provides context sensitive annotations from prior annotations and/or relevant prior images directly to the radiologist and/or the client annotation device 14 from a user input device 42 of the annotation manager 14 and/or allows images and/or image annotations to be viewed on a display device 44 of the annotation manager 14. The display device 44 can additionally or alternatively be used to facilitate receipt of images and/or image annotations from the user input device 42.

Figure 2:
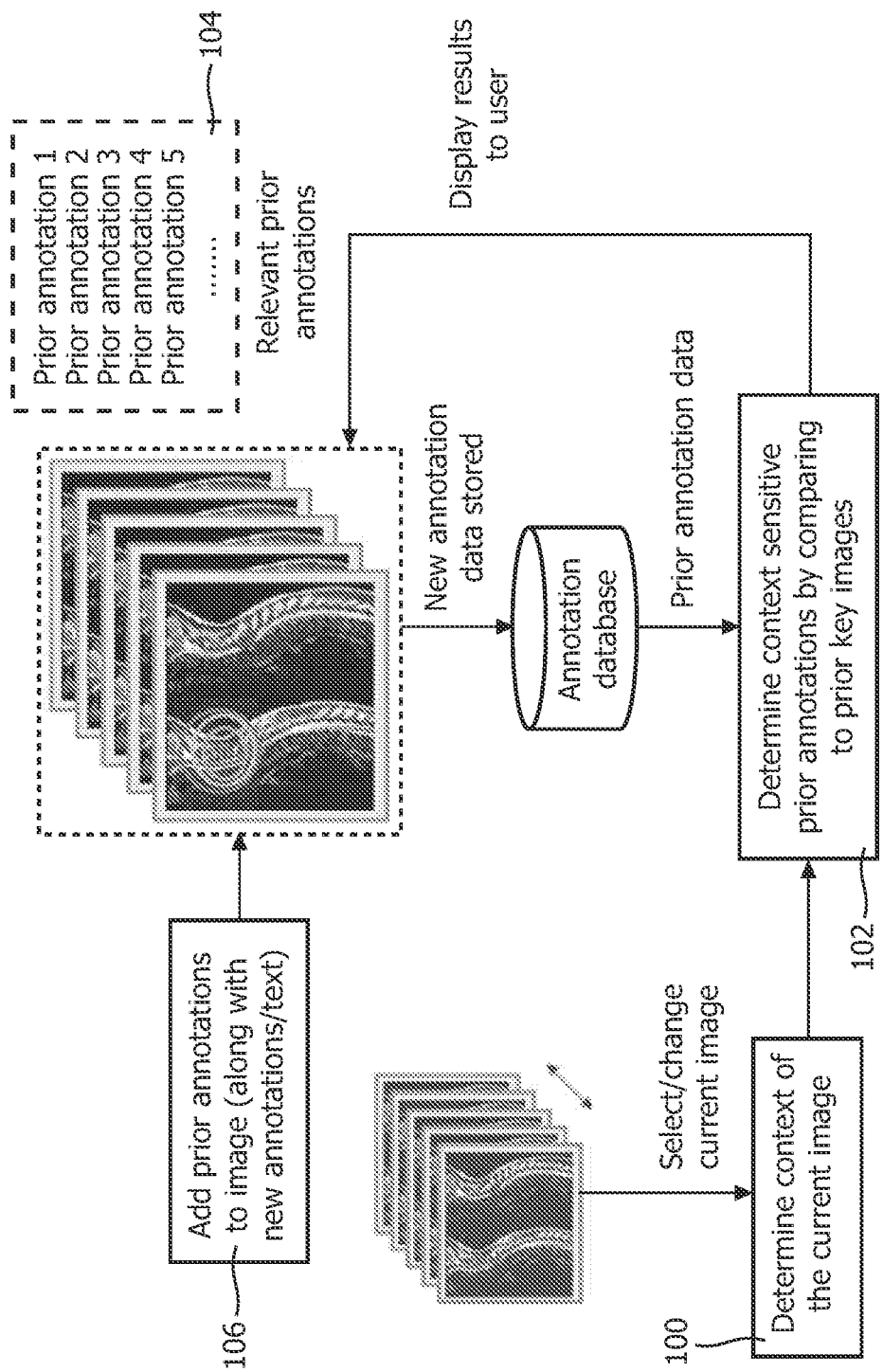
FIG. 2 illustrates a block-based visualization of an annotation support system according to aspects of the present application.

With reference to FIG. 2, a block-based visualization of an annotation support system is illustrated. In a block 100, the context extraction module 24, 36 automatically determines the context of an image currently being viewed by the radiologist. In one embodiment, the context extraction module 24, 36 extracts context information contained in a Digital Imaging and Communications in Medicine (DICOM) header of the image to determine the context of the image. DICOM is a standard for handling, storing, printing, and transmitting information in medical information. When an image is generated, a DICOM header is generated which contains information related to the modality of the imaging system and the body part being imaged. In another embodiment, a modal-based segmentation algorithm is applied to the current image. To determine the context of the current image, the context extraction module 24, 36 utilizing the model-based segmentation algorithm to extract information related to the body part and/or organs contained in the current image.

The context extraction module also automatically determines the context for new annotations being applied to an image currently being viewed by the radiologist. When a new annotation is added in the patient information system 16, the DICOM header of the image being annotated contains contextual information relevant to the annotation. This information is extracted using the context extraction module 24, 36 operation described in block 100 and associated with annotation such that the context of the current image corresponds to the context of the new annotation. The new annotation is then stored in the patient information system 16 along with the corresponding context information.

In a block 102, the matching module 26, 38 compares the current image context to contexts of images from prior studies. Prior contexts are retrieved from an annotation database 30, but alternatively, all prior image contexts can be determined 'on the fly'. The matching module 26, 38 utilizes the context information to determine which annotations are relevant. For example, the matching module 26, 28 utilizing the modality of the imaging system and body part being imaged to determine which annotations are relevant to the context of the current image. The matching module 26, 38 also utilizes the anatomy information to determine which annotations relate to the same organ being viewed by the radiologist on the image under investigation. Once the relevant key images are identified, the matching module 26, 38 retrieves the context sensitive annotations from the relevant images and displays them to the radiologist. In one embodiment, the context of images of prior studies is parsed utilizing known natural language processing methods. In another embodiment, the relevant images of prior studies are parsed to determine if the current study is a follow-up recommendation of the relevant previous study. In another embodiment, current clinical order data is parsed using natural language processing to determine the context of the current imaging data.

In a block 104, the display module 28, 40 displays a list of context sensitive annotations from prior reports. In one embodiment, the prior annotations are displayed in accordance with the radiologist's preferences. Each time a new annotation is created, it is added to the patient information system 16 and as such 'prior annotations' also include annotations that have been added to the current exam. The radiologist's preferences include listing all prior annotations (filtered only by modality and body part), listing all prior annotations made by the current radiologist, listing prior annotations made by the current radiologist only for the current patient (opposed to all annotations by current user), listing all prior annotations for the current patient (not only by current radiologist), and the like.

The prior annotation lists are utilized to display the list of related prior annotations that were found in block 104 to the radiologist. This list contains all the annotation related information and each use of the annotation related information is application specific. For instance, in an application focused on annotation reuse, the user could be given the option to select the prior annotation(s) of interest, and add either the entire annotation or only selected parts of it, such as only the description (used when a new shape needs to be associated with a prior description) or the shape is directly applied onto the current image.

In a block 106, the prior annotation(s) selected by the radiologist are added to the image along with any new annotations. Because some radiologists use different terms, types of annotations, etc., adding prior annotations cumulatively from a plurality of radiologists facilitates finding related images in further searches by others.

Figure 3:
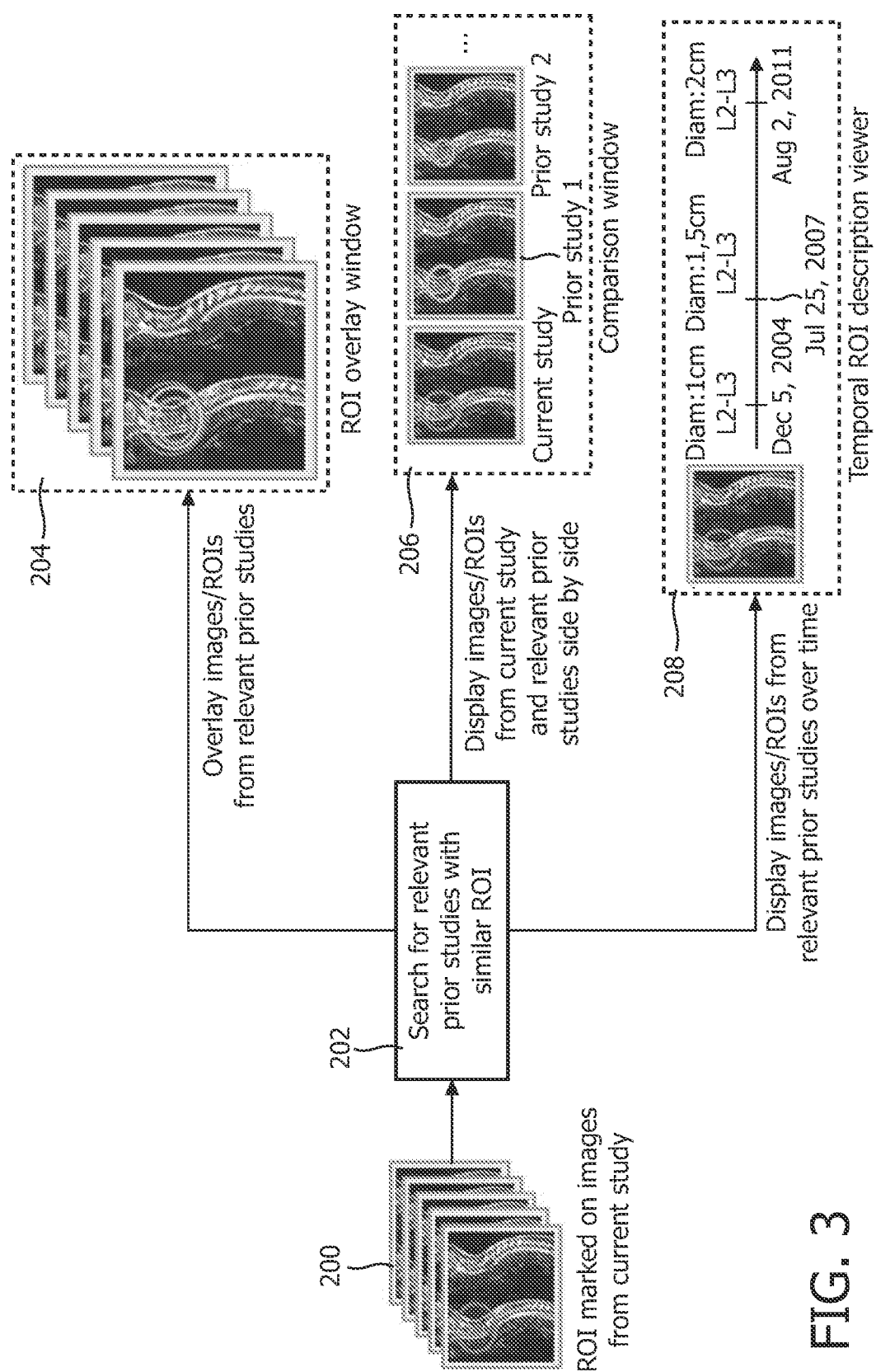
FIG. 3 illustrates a block-based visualization of another annotation support system according to aspects of the present application.

With reference to FIG. 3, a block-based visualization of another annotation support system is illustrated. In block 200, the context extraction module 24, 36 extracts context information for a ROI of a current image. In one embodiment, the context information is included in the DICOM header of the image containing the modality of the imaging system, the body part being imaged, information related to the current ROI (length/diameter for instance), and the like. In one embodiment, the context extraction module 24, 36 utilizes an image segmentation algorithm to identify the body part that resides/covers in the ROI as well as metadata encompassing a connection of pixel/voxel regions between imaging studies. In another embodiment, the image segmentation algorithms identify image characteristic of the lesion e.g., margin, shape, texture and elongation that are used to determine context more accurately.

In a block 202, the matching module 26, 28 automatically determines relevant annotations and prior studies. In one embodiment, the matching module 26, 38 performs a fast pass search where the matching module 26, 38 retrieves only annotations and prior studies that match the modality and body part of the current ROI (or by sorting). In another embodiment, the location of the ROI relative to the landmarks of the detected organ can be used to filter out irrelevant studies from the first fast pass performed. On a second pass, the matching module 26, 38 compares the measurable quantities of ROI (e.g., area, length of a lesion). A default threshold, i.e. ±10% or other value set by the radiologist, of the previous measure from the prior study findings can be used for the matching. In another embodiment, the characteristics of the ROI can be used to filter out irrelevant annotations from prior studies.

In order to ensure that correct prior studies are utilized in subsequent analysis, the matching module 26, 28 automatically displays a list of prior annotations and/or studies from the different prior studies to the radiologist. The radiologist is required to confirm the entries in a list. A checkbox checked by default is displayed against each list option and the radiologist can uncheck if a particular study is not relevant. For each prior study the radiologist confirms, an internal reference linking the current study and prior study is created.

In blocks 204, 206, 208 a display module 28, 40 systematically presents relevant, prior studies to the radiologist. Once the relevant prior studies have been confirmed by the radiologist per the previous step, the radiologist can compare/review all of these studies at once or select only a subset. For the selected studies, the radiologist can choose to: (a) overlay ROIs to do a visual comparison directly on the current study in a block 204, or (b) do a side-by-side comparison of studies in a block 206, (c) review the details related to each study along a temporal axis in a block 208 or (d) displaying the studies in temporal succession.

While the context extraction module 24, 36, a matching module 26, 38, and display module 28, 40 were shown as independent components, it is to be appreciated that each of the components can be part of an integrated client annotation device 12 and/or annotation manager 14. At least some of the components of the annotation support system 10 each include at least one processor 46, 48, 50 executing computer executable instructions from at least one memory 52, 54, 56 thereof. Components include the client annotations device 12, annotation device 14, and patient information system 16. The computer executable instructions embody the functionality of the components and include the applications of the client annotations device 12, annotation device 14, and patient information system 16. Further, at least some of the components each include a communication unit 58, 60, 62 and/or at least one system bus 64, 68. A communications unit provides a corresponding processor with an interface to at least one communication network, such as the communication network 18. A system bus allows the exchange of data between sub-components of the components. Sub-components include processors, memories, sensors, display devices, communication units, and so on.

Figure 4:
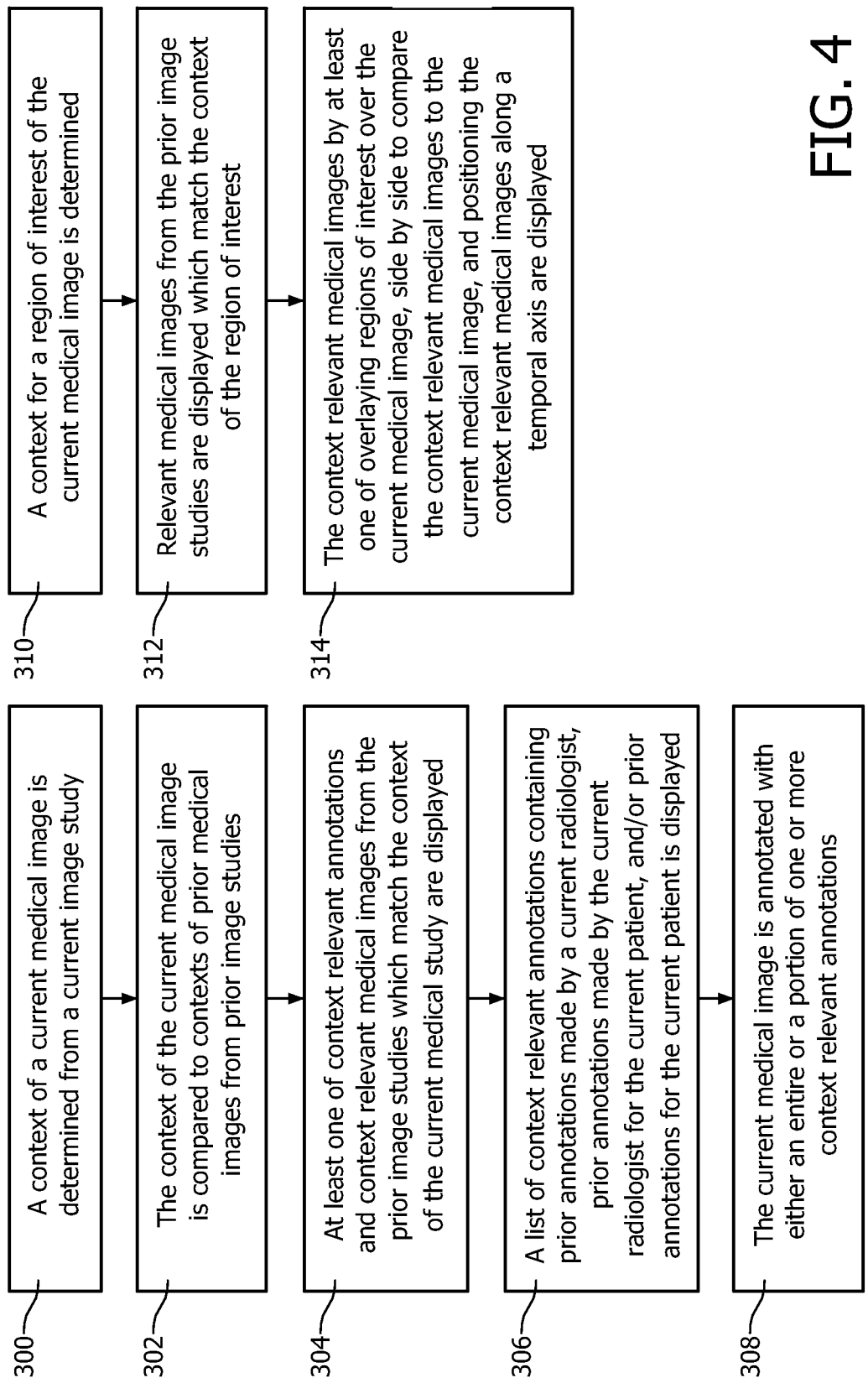
FIG. 4 illustrates a block diagram of a method of annotation support according to aspects of the present application.

With reference to FIG. 4, a block diagram of a method of annotation support is illustrated. In a step 300, a context of a current medical image is determined from a current image study. In a step 302, the context of the current medical image is compared to contexts of prior medical images from prior image studies. In a step 304, at least one of context relevant annotations and context relevant medical images from the prior image studies which match the context of the current medical study are displayed. In a step 306, a list of context relevant annotations containing prior annotations made by a current radiologist, prior annotations made by the current radiologist for the current patient, and/or prior annotations for the current patient is displayed. In a step 308, the current medical image is annotated with either an entire or a portion of one or more context relevant annotations. In a step 310, a context for a region of interest of the current medical image is determined. In a step 312, relevant medical images from the prior image studies are displayed which match the context of the region of interest. In a step 314, the context relevant medical images by at least one of overlaying regions of interest over the current medical image, side by side to compare the context relevant medical images to the current medical image, and positioning the context relevant medical images along a temporal axis are displayed.

As used herein, a memory includes one or more of a non-transient computer readable medium; a magnetic disk or other magnetic storage medium; an optical disk or other optical storage medium; a random access memory (RAM), read-only memory (ROM), or other electronic memory device or chip or set of operatively interconnected chips; an Internet/Intranet server from which the stored instructions may be retrieved via the Internet/Intranet or a local area network; or so forth. Further, as used herein, a processor includes one or more of a microprocessor, a microcontroller, a graphic processing unit (GPU), an application-specific integrated circuit (ASIC), a field-programmable gate array (FPGA), and the like; a user input device includes one or more of a mouse, a keyboard, a touch screen display, one or more buttons, one or more switches, one or more toggles, and the like; a database includes one or more memories; and a display device includes one or more of a LCD display, an LED display, a plasma display, a projection display, a touch screen display, and the like, including 3D-capable versions of these.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. An annotation support system, the system comprising:
   at least one display device;
   at least one processor programmed to:
   determine a context of a current medical image from a current image study;
   compare the context of the current medical image to contexts of prior medical images from prior image studies; and
   display context relevant annotations and context relevant medical images from the prior image studies which match the context of the current medical image,
   wherein the context includes a modality of the current image study, an identification of an anatomic region within the current image study, and a viewing orientation with respect to the anatomic region.

2. The annotation support system of claim 1, wherein the context is determined from at least one of context information contained in a header of the current medical image and information related to the anatomic region contained in the current medical image.

3. The annotation support system of claim 1, further programmed to display a list of context relevant annotations containing at least one of prior annotations made by a current radiologist, prior annotations made by the current radiologist for the current patient, and prior annotations for the current patient.

4. The annotation support system of claim 1, further programmed to overlay the context relevant annotations on the current medical image.

5. The annotation support system of claim 1, further programmed to annotate the current medical image with either an entire or a portion of one or more context relevant annotations.

6. The annotation support system of claim 1, further programmed to:
   associate the context of the current medical image with a context of a new annotation; and
   store the new annotation as a context relevant annotation.

7. The annotation support system of claim 1, further programmed to:
   determine a context for an annotation of a region of interest of the current medical image; and
   display relevant medical images from the prior image studies which match the context of the region of interest.

8. The annotation support system of claim 1, further programmed to control a display device to display the context relevant medical images by at least one of overlaying regions of interest over the current medical image, side by side to compare the context relevant medical images to the current medical image, and display the context relevant medical images on a temporal axis.

9. A method of providing annotation support, the method comprising:
   determining a context of a current medical image from a current image study or a context for an annotation of a region of interest of the current medical image;
   comparing the context of the current medical image to contexts of prior medical images from prior image studies; and
   displaying context relevant annotations and context relevant medical images from the prior image studies which match the context of the current medical image,
   wherein the context of a current medical image from a current image study includes a modality of the current image study, an identification of an anatomic region within the current image study, and a viewing orientation with respect to the anatomic region.

10. The method according to claim 9, wherein determining the context includes determining from at least one of context information contained in a header of the current medical image and information related to the anatomy of contained in the current medical image.

11. The method according to claim 9, further including displaying a list of context relevant annotations containing prior annotations made by a current radiologist, prior annotations made by the current radiologist for the current patient, and/or prior annotations for the current patient.

12. The method according to claim 9, further including cumulatively annotating the current medical image with either an entire or a portion of one or more context relevant annotations.

13. The method according to claim 9, further including:
   determining a context for a region of interest of the current medical image; and
   displaying relevant medical images from the prior image studies which match the context of the region of interest.

14. The method according to claim 9, further including displaying the context relevant medical images by at least one of overlaying regions of interest over the current medical image, side by side to compare the context relevant medical images to the current medical image, and positioning the context relevant medical images along a temporal axis.

15. The method of claim 9, wherein the context relevant annotations include an annotation of a region of interest of the current medical image that includes visual information including at least one of shape, dimension, margin, texture, and elongation of a feature within the region of interest.

16. The system of claim 1, wherein the context relative annotations include at least one annotation related to a diagnostic assessment of the current medical image.

17. The system of claim 1, wherein the context relative annotations include an identification of a region of interest in the current medical image.

18. A non-transitory computer readable medium that includes a program that, when executed by a processing system causes the processing system to:
- determine a context of a current medical image from a current image study;
- compare the context of the current medical image to contexts of prior medical images from prior image studies; and
- display context relevant annotations and context relevant medical images from the prior image studies which match the context of the current medical image;
- wherein the context includes a modality of the current image study, an identification of an anatomic region within the current image study, and a viewing orientation of the anatomic region.

19. The medium of claim 18, wherein the program further causes the processing system to display a list of context relevant annotations containing at least one of prior annotations made by a current radiologist, prior annotations made by the current radiologist for the current patient, and prior annotations for the current patient.

20. The medium of claim 18, wherein the context includes a region of interest within the current medical image.

* * * * *